United States Patent
Paul et al.

(10) Patent No.: US 11,654,292 B2
(45) Date of Patent: May 23, 2023

(54) TARGETED OSMOTIC LYSIS OF MALIGNANT CANCER CELLS USING PULSED MAGNETIC FIELD GRADIENTS

(71) Applicant: Board of Supervisors of Louisiana State University and Agricultural and Mechanical College, Baton Rouge, LA (US)

(72) Inventors: Dennis J. Paul, New Orleans, LA (US); Harry J. Gould, III, New Orleans, LA (US)

(73) Assignee: Board of Supervisors of Louisiana State University and Agricultural and Mechanical College, Baton Rouge, LA (US)

(*) Notice: Subject to any disclaimer, the term of this patent is extended or adjusted under 35 U.S.C. 154(b) by 609 days.

(21) Appl. No.: 16/632,034

(22) PCT Filed: Jul. 12, 2018

(86) PCT No.: PCT/US2018/041894
§ 371 (c)(1),
(2) Date: Jan. 17, 2020

(87) PCT Pub. No.: WO2019/018207
PCT Pub. Date: Jan. 24, 2019

(65) Prior Publication Data
US 2020/0147405 A1 May 14, 2020

Related U.S. Application Data

(60) Provisional application No. 62/696,702, filed on Jul. 11, 2018, provisional application No. 62/534,947, filed on Jul. 20, 2017.

(51) Int. Cl.
| | | |
|---|---|---|
| *A61N 2/02* | (2006.01) | |
| *A61B 5/05* | (2021.01) | |
| *A61P 35/00* | (2006.01) | |
| *A61K 31/352* | (2006.01) | |
| *A61K 31/7048* | (2006.01) | |

(52) U.S. Cl.
CPC ............... *A61N 2/02* (2013.01); *A61B 5/05* (2013.01); *A61K 31/352* (2013.01); *A61K 31/7048* (2013.01); *A61P 35/00* (2018.01)

(58) Field of Classification Search
CPC ..................... A61N 2/02; A61B 5/05
See application file for complete search history.

(56) References Cited

U.S. PATENT DOCUMENTS

| 7,769,462 B2 | 8/2010 | Meadows | |
| 8,921,320 B2 * | 12/2014 | Paul | A61K 45/06 |
| | | | 514/17.4 |
| 2010/0125191 A1 * | 5/2010 | Sahin | G01R 33/48 |
| | | | 600/422 |
| 2013/0102881 A1 | 4/2013 | Miyazaki | |
| 2015/0080327 A1 | 3/2015 | Paul | |

FOREIGN PATENT DOCUMENTS

| JP | 2014-520890 A | 8/2014 |
| WO | 2013/012997 A1 | 1/2013 |

OTHER PUBLICATIONS

Wang et al. Expert Opin. Ther. Patents 2012, 22, 587-605 (Year: 2012).*
Ahmed et al. Bioelectromagnetics 2015, 36, 386-397 (Year: 2015).*
Wang, Hy et al. Modulators of Na/K-ATPase: a patent review. Expert Opinion on Therapeutic Patents, vol. 22, No. 6, May 17, 2012 pp. 587-605.
Alphandery, E et al. Chains of Magnetosomes Extracted from AMB-1 Magnetotactic Bacteria for Application in Alternative Magnetic Field Cancer Therapy. ACS Nano, American Chemical Society, vol. 5, No. 8, 2011, pp. 6279-6296 [online], [retrieved on Aug. 27, 2018] Retrieved from the Internet <URL: https://hal.sorbonne-universite.fr/hal-01547088/ document>.
International Search Report for PCT application No. PCT/US18/41894, dated Sep. 18, 2018.
Written Opinion of the International Searching Authority for PCT application No. PCT/US18/41894, dated Sep. 18, 2018.
Aleizopoulos, K, et al., Na+/K+ ATPase Inhibitors in Cancer. Current Drug Targets, 2014, 15, 988-1000.
Database Embase Elsevier "Targeted osmotic lysis of higly invasive carcinomas using a pulsed magnetic field and pharmacological blockade of voltage-gated sodium channels", 2018.
Extended European Search Report, dated Feb. 19, 2021, in the corresponding European patent application No. 18835073.0.
Maggi, et al., "Digoxin Mediated Electromagnetically Induced Targeted Osmotic Lysis in Cancer Cells", Medical Physics, vol. 44, No. 6, Jun. 2017, pp. 2975-2976.
Notice of Reasons for Refusal received for Japanese Patent Application Serial No. 2020524716 dated Jul. 19, 2022, 13 pages (7 page of English Translation and 6 page of Official Copy).
Yuhi, et al., "Repetitive Transcranial Magnetic Stimulation Enhances the Activities of Voltage-Dependent Na Channels in Rat Brain", Japanese Journal of Pharmacology, Abstract No. P-617, 2002, 216 page.

\* cited by examiner

*Primary Examiner* — Matthew P Coughlin
(74) *Attorney, Agent, or Firm* — Wiley Rein LLP

(57) ABSTRACT

Methods are provided for targeting cancer cells that overexpress voltage-gated sodium channels (VGSCs or "sodium channels") and causing osmotic lysis of these cancer cells by initially inhibiting the sodium, potassium-adenosine triphosphatase ($Na^+$, $K^+$-ATPase or "sodium pump"), and then stimulating the VGSCs by pulsed magnetic field gradients to cause sodium and water to enter the cancer cells.

18 Claims, 5 Drawing Sheets

Grade 1    Grade 2.5    Grade 4

Kidney

Spleen

Skin

Tumor + Muscle

TARGETED OSMOTIC LYSIS OF MALIGNANT CANCER CELLS USING PULSED MAGNETIC FIELD GRADIENTS

RELATED APPLICATION

This Application is a § 371 National Stage Application of PCT/US2018/041894, filed Jul. 12, 2018, which claims priority benefit to U.S. Provisional Application No. 62/534,947, filed Jul. 20, 2017, and U.S. Provisional Application No. 62/696,702, filed Jul. 11, 2018, both of which are fully incorporated herein by reference for all purposes.

FIELD

The present disclosure relates to methods for targeting cancer cells that over-express voltage-gated sodium channels (VGSCs or "sodium channels") and to cause osmotic lysis of these cancer cells by inhibiting the sodium, potassium-adenosine triphosphatase ($Na^+$, $K^+$-ATPase or "sodium pump"), and stimulating the VGSCs by pulsed magnetic field gradients to cause sodium and water to enter the cancer cells.

BACKGROUND

Chemotherapy and radiotherapy of metastatic cancer, because of toxicity to both normal and abnormal tissues, present the clinician with the difficult challenge of trying to kill the neoplastic disease before killing the patient; a balance between treatment and rescue. All traditional cancer treatments are associated with toxicity, an increase in morbidity, and a reduction in quality of life that may extend far beyond the period of treatment. A major focus of current anti-neoplastic treatments is targeting treatment to the cancer cells, for example, targeting proteins expressed or over-expressed by cancer cells, but not by normal tissue.

Many invasive cancer cell types over-express VGSCs by more than 1000-fold greater than normal cells. Cancer cells that over-express VGSCs are epithelial carcinomas that include, but are not limited to, highly invasive breast cancer, prostate cancer, small cell lung cancer, non-small cell lung carcinoma, lymphoma, neuroblastoma, and cervical cancer. Some sarcomas, notable rhabdomyosarcoma, mesothelioma, osteosarcoma, also overexpress VGSCs. Mesothelioma not classified as an epithelial cancer is also known to over-express VGSCs. When these sodium channels are activated, $Na^+$ is conducted into the cells. In these cancers, the degree of metastasis is directly related to an increased expression of VGSCs. Physiologically, these cancer cells share certain cellular properties with normal excitable cells such as neurons and cardiac myocytes (for example, the conduction of action potentials). U.S. Pat. No. 7,393,657 discloses the use of inhibitors of VGSCs as a treatment for cancer, including breast cancer.

Of the 1.6 million people contracting epithelial cell cancer each year in the U.S., 40% are considered to be "highly invasive" and over-express VGSCs. These patients diagnosed with malignant/metastatic carcinomas are treated currently with major and often disfiguring surgical procedures, chemotherapy and/or radiation. More than 400,000 people die from epithelial cell carcinoma each year in the United States and an estimated 10 times that worldwide. In addition, another 1.2 million U.S. patients diagnosed with invasive cancer are successfully treated with traditional surgery, chemotherapy and/or radiation. Breast cell carcinoma is an example of a highly invasive cancer. More than 40,000 people die from breast cell carcinoma each year in the United States and 465,000 worldwide. Greater than 90% of these deaths are due to metastasis of the primary tumor. In addition, another 170,000 U.S. women diagnosed with invasive breast cancer are successfully treated with traditional mastectomy, lumpectomy, chemotherapy and/or radiation. Of the 207,000 people contracting breast cancer each year, 40% of the cancers are considered to be "highly invasive", and over-express VGSCs.

The family of sodium channels named "voltage-gated sodium channels" was so designated due to the sensitivity to small changes (about 30 mV; from a resting membrane potential of −70 mV to threshold of −40 mV) in the voltage across the cellular membrane. They have also been shown to be activated by many forms of stimulation—electric current, mechanical disturbances in the membrane, ultrasound, magnetic fields, and several drugs. There are nine members of the VGSC family, with nine different isoforms. They are designated $Na_v1.X$, where X represents 1–9. One different channel, NaX, does not respond to shifts in voltage, but to extracellular sodium concentrations.

$Na^+$, $K^+$-ATPase is a ubiquitous transmembrane protein in animal cells, and functions to maintain an ion imbalance across the cell membrane where more charged ions are located outside of the cell, largely sodium ions, than inside. This produces an electrochemical gradient that is in homeostatic balance. When ionic imbalance shifts in the presence of a change in voltage an action potential is generated causing a transient osmotic shift toward an intracellular hypertonic state. The restoration of the sodium imbalance is an essential function performed by $Na^+$, $K^+$-ATPase. When $Na^+$, $K^+$-ATPase does not function properly, water follows sodium into the cell to restore osmotic balance thereby increasing cell volume. In normal cells this shift in cell volume is tolerated due to membrane compliance. Blocking $Na^+$, $K^+$-ATPase function can lead to a loss of cellular excitability and an increase in cellular volume. Many inhibitors are known, including the cardiac glycosides. The isozymes vary in their sensitivity to each of the cardiac glycoside drugs. More than 30 drugs have been shown to inhibit sodium pump activity. These include ouabain, digitalis, and its active ingredients digoxin and digitoxin.

U.S. Patent Application Publication No. 2007/0105790 discloses the use of cardiac glycosides (e.g., ouabain and proscillaridin) either alone or in combination with other standard cancer therapeutic agents to treat pancreatic cancers by causing cell apoptosis. U.S. Patent Application Publication No. 2009/0018088 discloses the use of cardiac glycosides, including digoxin and ouabain, to induce cell apoptosis as a treatment for cancer.

U.S. Pat. No. 8,921,320 discloses methods for treating cancer in a mammal involving co-administering to tumor cells that over-express voltage-gated sodium channels a first agent and a second agent, wherein the first agent inhibits $Na^+$, $K^+$-ATPase, and wherein the second agent stimulates voltage-gated sodium channels, to cause the osmotic lysis of the tumor cells, resulting in a substantial reduction in tumor cell viability within about one hour after said co-administration. In this regard, highly malignant cancer cells may be selectively killed by blocking sodium pumps and simultaneously stimulating the opening of sodium channels in these cells. The first agents may include ouabain, or digitoxin, and the second agents may include electrical current, ultrasound, magnetic field, or drug compounds such as veratridine.

A need exists for improved mechanisms and techniques for providing magnetic stimulation to achieve targeted osmotic lysis of malignant cancer cells.

SUMMARY

The aspects and embodiments of the present disclosure provide methods for targeted osmotic lysis (TOL) of cancer cells that over-express voltage-gated sodium channels (VGSCs or "sodium channels") and to cause osmotic lysis of these cancer cells by inhibiting the sodium, potassium-adenosine triphosphatase ($Na^+$, $K^+$-ATPase or "sodium pump"), and stimulating the VGSCs by pulsed magnetic field gradients to cause sodium and water to enter the cancer cells.

Certain embodiments of the disclosure relate to methods for TOL of cancer cells that over-express VGSCs by stimulating the VGSCs by a z-gradient magnetic field in the presence of the static field magnet with a ramp rising from −90 mV to −30 mV over a rising time of about 0 to 20 msec, an inter-pulse interval of about 7.5 to 30 msec, and a pulse cycle frequency of about 20-60 PPS. In a preferred embodiment, the pulsed magnetic field is a z gradient magnetic field with a ramp rising from −90 mV to −30 mV over a rising time of about 10 msec, returning to base over 2.5 msec, an inter-pulse interval of 7.5 msec, and a pulse cycle frequency of 25 PPS. The pulsed magnetic field reaches stimulus intensity at 80 mT to produces close to 100% cell lysis.

DETAILED DESCRIPTION

Figure 1:
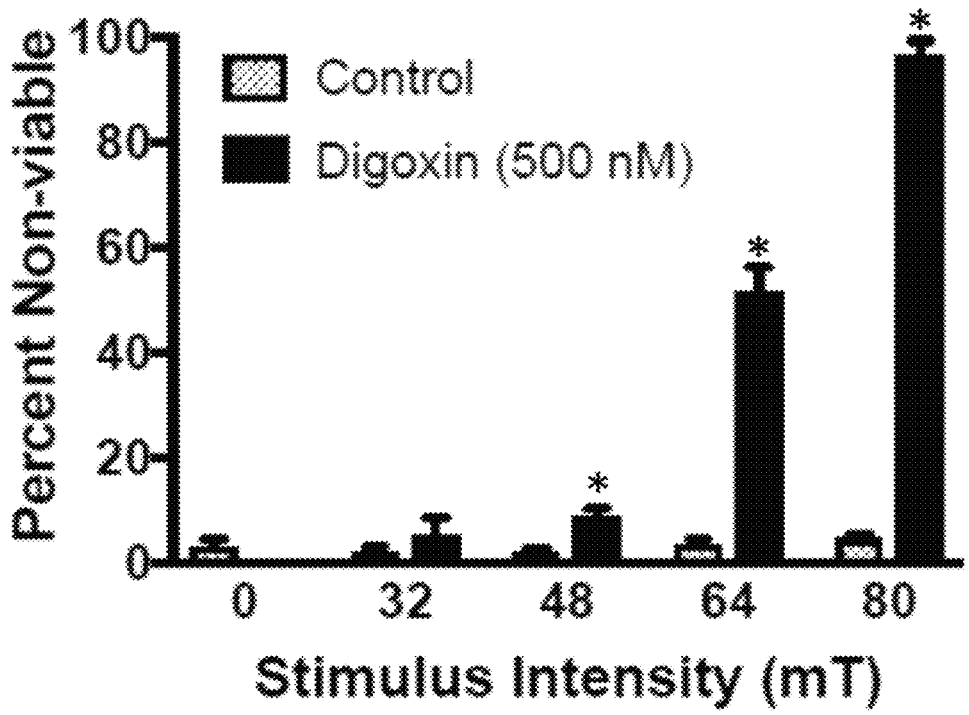
FIG. 1 Stimulus intensity—response curve to determine the strength of the pulsed magnetic field necessary to produce cell lysis of MDA-MB-231 cells, in vitro ($p<0.01$).

All patents and other publications identified are incorporated herein by reference for the purpose of describing and disclosing, for example, the methodologies described in such publications that might be used in connection with the present invention, but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

As used herein and in the claims, the singular forms "a," "an," and "the" include the plural reference unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Other than in the operating examples, or where expressly stated or otherwise indicated, all numbers expressing quantities of ingredients or reaction conditions used herein should be understood as modified in all instances by the term "about."

Unless defined otherwise, all technical and scientific terms used herein have the same meaning as those commonly understood to one of ordinary skill in the art. The terminology used herein is for the purpose of describing particular embodiments only, and is not intended to limit the scope of the present invention, which is defined solely by the claims. The terms male and female may be used interchangeably to describe corresponding components or complementary aspects thereof and are not a limitation to either particular structure unless context clearly indicates otherwise.

Headings are provided for convenience only and are not to be construed to limit the invention in any way. Unless defined otherwise, all technical and scientific terms used herein have the same meaning as those commonly understood to one of ordinary skill in the art. The terminology used herein is for the purpose of describing particular embodiments only, and is not intended to limit the scope of the present invention, which is defined solely by the claims. In order that the present disclosure can be more readily understood, certain terms are first defined. Additional definitions are set forth throughout the detailed description.

Targeted osmotic lysis (TOL) has many advantages over traditional cancer therapies. Chemotherapy typically causes damage in healthy, as well as cancerous, tissue, leading to lengthy recovery and chronic morbidity. By comparison, TOL will destroy only cells that over-express VGSCs. Thus, a more selective lesion of diseased tissue is expected. This will contribute to fewer long-term adverse effects of treatment. Radiation therapy is typically directed to kill the healthy tissue surrounding the cancerous tissue. Like chemotherapy, this often leads to lengthy recovery and chronic morbidity. Because of the selectivity of TOL for cells that over-express VGSCs, there is little to no peri-neoplastic damage.

The present disclosure provides methods for targeting cancer cells that over-express voltage-gated sodium channels (VGSCs or "sodium channels") and to cause osmotic lysis of these cancer cells by inhibiting the sodium, potassium-adenosine triphosphatase ($Na^+$, $K^+$-ATPase or "sodium pump"), and stimulating the VGSCs by pulsed magnetic field gradients to cause sodium and water to enter the cancer cells. The magnetic stimulation, for example, may be used to produce depolarization between about −90 mV and −30 mV in vitro.

Sodium channels are responsible for the rising phase of the neuronal action potential. The average resting membrane potential for neurons is −70 mV, for skeletal muscle, −90 mV, and for epithelial cells, −50 mV. The peak of the action potential is +40 mV. After the peak, the channels close, and there is a variable period of recovery during which time another action potential cannot be initiated, i.e., the refractory period. The opening, closing and reprising of the channels seems to be subtype specific rather than cell type specific. Larger depolarizations are associated with rapid sodium channel opening and slower inactivation, i.e., more sodium influx. Sodium entry initially flows down the charge gradient to 0 mV, then to +40 mV down the concentration gradient.

There are nine known isoforms of voltage-gated sodium channel. Opening of the isoforms varies between −90 mV and −30 mV. Some isoforms open slowly at pre-threshold levels, −80 mV to −60 mV, and close slowly providing leak currents, which may be a mechanism for stimulus summation. Other isoforms open rapidly at threshold potentials. Channel isoforms reprime or recover from stimulation at different rates, which allows for rapid firing (nerve impulses) or constant, regular firing (cardiac muscle). The average time for depolarization is 10 to 20 msec. The full recovery from inactivation is about 45 msec.

Where electrical stimulation has been used in targeted osmotic lysis, the parameters have included: (A) in vitro—1.0 V DC, 1 msec pulse, 15 pps for up to 5 min; and (b) in vivo—10 V DC, 1 msec pulse, 15 pps for 2.5 min, then rotating electrode pair 90° and stimulating again for 2.5 min.

The present disclosure provides for embodiments using magnetic stimulation in targeted osmotic lysis. The parameters may include: ramp rise time from −90 mV to −30 mV over 10 msec, return to base 2.5 msec, and inter-pulse interval of 7.5 msec, pulse cycle frequency 25 PPS i.e., 20 msec/pulse cycle, delivered in difference gradient planes. The ramp may range from about 0 to about 20 msec, and the inter-pulse interval may range from about 15 to about 30 msec. In some embodiments, the pulse cycle frequency may be about 20-60 PPS. In an embodiment, the parameters may include: a wave form with a 12.5 msec ramp rise time, a 7.5 msec plateau and a 12.5 msec return to baseline where the inter-pulse interval is 7.5 msec with a pulse frequency range between about 25-50 PPS.

As used herein, "magnetic field" refers to the magnetic effect of electric currents and magnetic materials. A magnetic field may be generated when electric charge carriers such as electrons move through space or within an electrical conductor. The geometric shapes of the magnetic flux lines produced by moving charge carriers (electric current) are similar to the shapes of the flux lines in an electrostatic field. A magnetic field may be generated by various devices, including a magnetic resonance imaging device. Apparatuses and systems for magnetic resonance imaging have been described. See, e.g., U.S. Pat. Nos. 5,779,637, 5,666, 056, and 4,411,270. For example, a doughnut shaped superconducting magnet or a copper wound ambient temperature electromagnet may provide a primary static magnetic field.

A suitable apparatus and system for the generation of a magnetic field stimulation includes a device consisting of toroidal or solenoid wound hardware and enclosure, a current driving stage and power supply, a mechanism for adjusting magnetic pulse and wave forms developed on a microcontroller and a circuit board design, software drivers and user interface. The Pulse waveform will be controlled with a microcontroller that will generate a Pulse-Width-Modulated (PWM) signal that will be used to drive a Class-D style electronic amplifier, which will in turn drive current through the toroidal windings. The device will generate the designed electric field pulses in the empty bore and deliver 0.2-0.9 Tesla field strength.

Non-limiting examples of pharmaceutical compounds that can be used to block $Na^+$, $K^+$-ATPase include ouabain (g-Strophantin); dihydroouabain; ouabain octahydrate; ouabagenin; digoxin; digitoxin; digitalis; acetyldigitoxin; acetyldigoxin; lanatoside C; deslanoside; metildigoxin; gitoformate; oleanderin; oleandrigenin; bufotoxin; bufotalin; marinobufagenin (3,5-dihydroxy-14,15-epoxy bufodienolide); palytoxin; oligomycins A, B, C, E, F, and G; rutamycin (oligomycin D); rutamycin B; strophanthin (g-strophanthin, Acocantherine); k-β-strophanthin; strophanthidin; k-strophanthoside; cymarin; erysimoside (cardenolide); helveticoside; peruvoside; hypothalamic $Na^+$, $K^+$-ATPase inhibitory factorn (HIF); the aglycone of HIF; arenobufagin; cinobufagin; marinobufagin; proscillaridin; scilliroside; daigremontianin; 3, 4, 5, 6-tetrahydroxyxanthone; and all other inhibitors of $Na^+$, $K^+$-ATPase, combinations and derivatives of each.

The $Na^+$, $K^+$-ATPase blocker may be delivered to a single tumor via direct or intravenous administration, to a single organ or area via intravenous or intraluminal administration, or the entire body via intravenous, subcutaneous intramuscular or oral administration. Magnetic field stimulation of sodium channels can be delivered to a single tumor, a single organ, a section of the body, or the entire body. All types and subtypes of the VGSCs family should be equally susceptible to this technology. For example, cell lines that over-express $Na_v1.1$, $Na_v1.2$, $Na_v1.5$, $Na_v1.5a$ and $Na_v1.7$ are susceptible to mediated targeted lysis.

EXAMPLES

It should be understood that the examples and embodiments described herein are for illustrative purposes only and that various modifications or changes in light thereof will be suggested to persons skilled in the art and are to be included within the spirit and purview of this application and the scope of the appended claims. All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Example 1

MRI In Vitro Study in Vials Containing Pellets of Live and Alcohol-Killed Malignant Breast Cancer Cells Baseline images of cultured, normal control and alcohol-killed malignant breast cancer cells (MDA-MB-231) were obtained with a magnetic resonance imaging (MRI) apparatus and system to assess any difference between live and killed cells with MRI. For this study, three vials of cells were used to provide enough cells to form an easily visualized pellet when imaged. Cell numbers in a single vial were insufficient to form a pellet large enough to clearly discern a difference. The cells were placed in micro-centrifuge tubes and centrifuged to form pellets. The tubes were then placed side-by-side in the MRI at the calculated center of the field and scanned. A clear difference between the tubes was observed.

A magnetic stimulation set of parameters was selected, which involved the generation of a magnetic field pulse in the z-gradient using a rise time of 10 msec to attain an amplitude of 187.5973, followed by a 2.5 msec return to baseline and an inter-stimulus interval of 17.5 msec. The gradient field was pulsed for 5 min.

Example 2

Results of In Vitro Studies in Ouabain-Treated (TOL) Malignant Breast Cancer Cells Exposed to Pulsed Magnetic Field Stimulation in the z-Gradient Two tubes of MDA-MB-231 cells were prepared. The media in one tube was replaced by media containing 100 nM ouabain to block the sodium pumps. Both tubes were placed in the MRI and offset from center by 317 mm in the z-gradient field and exposed to the pulsed magnetic field. The samples were then repositioned and imaged. Magnetic resonance imaging of vials containing pellets of control MDA-MB-231 cells and ouabain-treated (TOL) MDA-MB-231 cells that had been exposed to pulsed magnetic field stimulation in the z-gradient for 5 min displays observable difference.

After imaging, the cells in each vial were stained with Trypan Blue to estimate the number of cells that had been lysed by each treatment: (A) magnetic stimulation alone or (B) ouabain and magnetic stimulation. Virtually all of the cells that had only been exposed to pulsed magnet field stimulation were alive (expelled the Trypan Blue stain) and 10-15% of the cells that had been simultaneously treated with ouabain and pulse magnetic field stimulation were dead (appeared shrunken and retained the stain).

In this example, cells were exposed to ouabain for over 60 min during the preparation for the magnetic field stimulation. Because lysis may occur in a small percentage of cells when exposed to ouabain alone, a study was conducted where a vial of cells was exposed to ouabain without pulsed field stimulation for greater than 90 min. Less than 1% of the cells exposed to ouabain alone for this period of time were found to be dead, which reflected similar kill rates where cells were exposed to ouabain for 10 min.

The duration, amplitude and frequency of the pulsed z-gradient field was varied. All targeted osmotic lysis (TOL) vials (ouabain and pulsed magnetic field stimulation) were exposed to 100 nM ouabain for 10 min. Ouabain-treated and normal MDA-MB 231 control vials were exposed to the same pulsed magnetic field and then stained with Trypan Blue to estimate the amount of cell lysis in each tube. Two trials were conducted using the maximum field strength available (289.1689 Amp). The pulsed stimulus for the first of these trials was delivered with a rise time of 10 msec, a 2.5 msec return to baseline and an inter-stimulus interval of 17.5 msec; the stimulus was pulsed with a rise time of 10 msec, a 2.5 msec return to baseline and an inter-stimulus interval of 7.5 msec for the second trial. An additional trial was run with stimulus amplitude of 187.5973 Amp, but unlike the other trial, the rise time of 10 msec, a 2.5 msec return to baseline and an inter-stimulus interval of 7.5 msec was used to further assess the contribution of stimulus frequency on cell lysis. A favorable cell lysis, e.g., 80-90% kill rate, was found when the field amplitude was 289.1689 and the inter-pulse interval was 7.5 msec (50 Hz).

Example 3

Results of In Vitro Studies in Digoxin-Treated (TOL) Malignant Breast Cancer Cells Exposed to Pulsed Magnetic Field Stimulation in the z-Gradient MDA-MB-231 breast cancer cells, cultured in DMEM, or MCF-10a normal breast epithelial cells, cultured in mammary epithelial growth medium (MEGM; Lonza, www.lonza.com), were dissociated with Corning Cellstripper (Corning, N.Y.) and resuspended in 1.5 ml microfuge tubes using DMEM with or without 100 nM digoxin (SigmaAldrich). Tubes were placed in an 8"1X 2.5"dia. solenoid with 697 turns (500 ft.) of 12 ga copper wire. A 5VDC current from an AE Techron 7224 DC-extended AC amplifier pulsed at 25 Hz, with a 10 msec ramp and fall, controlled by a Techtronics AFG 3021B waveform generator produced 80 mT magnetic pulses in the solenoid. Of the digoxin treated MDA-MB-231 cells, 97.5% lysed within 10 min, whereas in no-drug controls, only 4.5% were non-viable. Neither digoxin-treated nor untreated MCF-10a cells lysed when stimulated.

Example 4

Simultaneous Pulsing of the x-, y- and z-Gradient Fields on Targeted Osmotic Lysis A study was conducted to assess the effect of simultaneous pulsing of the x-, y- and z-gradient fields on targeted osmotic lysis. Cell vials were prepared as described above. The wave forms presented were identical in each gradient field and were all pulsed for 5 minutes, but varied between trials with respect to amplitude and frequency. The amplitudes used were the maximum amplitudes allowed by the system to deliver a pulse train of 5 min in duration. The system would automatically shut down at higher amplitudes. One trial involved an amplitude of 262.4531, a rise time of 10 msec, a return to baseline of 2.5 msec and an inter-pulse interval of 17.5 msec. Another trial involved an amplitude of 224.9519, a rise time of 10 msec, a return to baseline of 2.5 msec and an inter-pulse interval of 7.5 msec. And yet another trial involved an amplitude of 206.2014, a rise time of 10 msec, a return to baseline of 2.0 msec and an inter-pulse interval of 3.0 msec. Cell lysis was significantly less than an 80-90% kill rate, when the three gradient fields were pulsed together than when the z-gradient field was pulsed alone.

Example 5

A Study in Cells Pulsed with a z-Gradient Field in the Absence of the Static Field Magnet A study was conducted where cells were pulsed with a z-gradient field in the absence of the static field magnet. The cytologic assessment of the amount of cell lysis of MDA-MB-231 cells obtained with the static field was significantly greater than the amount of lysis obtained without the presence of the static field.

Example 6

A Study of Stimulus Intensity—Response Curve to Determine the Strength of the Pulsed Magnetic Field Necessary to Produce Cell Lysis of MDA-MB-231 Cells In Vitro A study was conducted where cells were pulsed with an increasing stimulus intensity to determine the strength of the pulsed magnetic field necessary to produce cell lysis of MDA-MB-231 cells in vitro. Cells were distributed to microfuge tubes with or without 500 nM digoxin. All tubes were exposed to a 0 to 80 mT PMF. FIG. 1 shows that stimulus intensity at 80 mT produces close to 100% cell lysis of MDA-MB-231 cells.

Example 7

Figure 2:
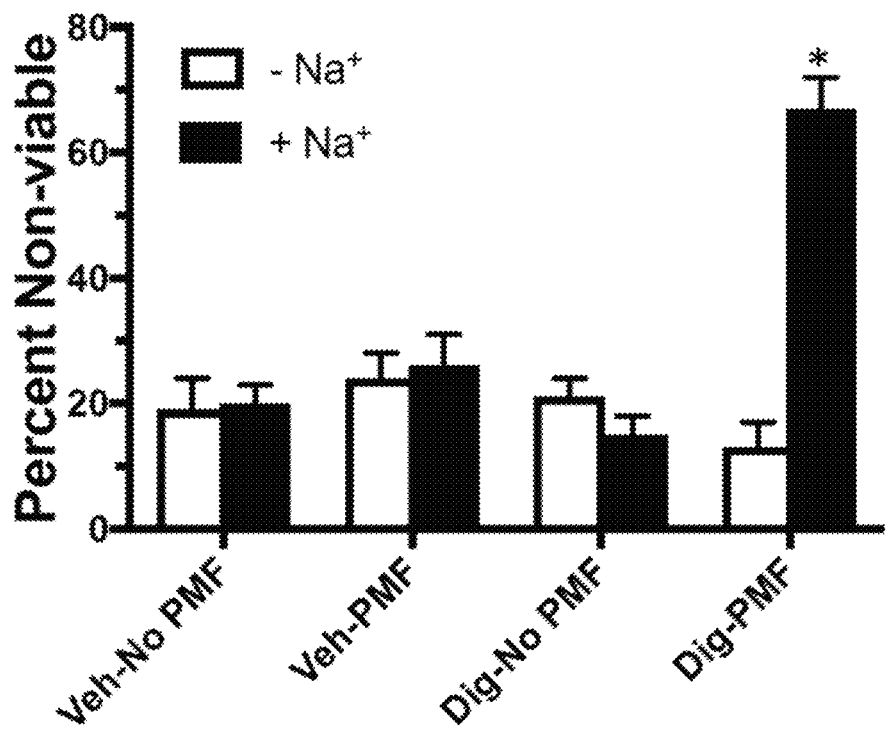
FIG. 2 TOL is dependent on the presence of sodium. The bar graph shows that in the presence of sodium, digoxin and PMF (filled bar, Dig-PMF) cell lysis occurs, whereas in the absence of sodium, TOL (empty bar, Dig-PMF), cell lysis does not occur ($p<0.01$).

A Study of the Association of the Presence of Sodium and the Efficacy of TOL A study was conducted where the culture media containing MDA-MB-231 cells was replaced with Ringer's solution with or without sodium and then stimulated with pulsed magnetic fields of 80 mT for 10 minutes. Cells were transferred to microfuge tubes containing either Ringers +$Na^+$ or Ringers−$Na^+$. Tubes in each of these media received one of four treatments: the Ringers vehicle and no stimulation (VEH-No PMF); vehicle and the 80 mT PMF (Veh-PMF); 500 nM digoxin and no stimulation (Dig-No PMF); and digoxin with the PMF stimulation (Dig-PMF), received no digoxin and were stimulated (Veh-PMF) or not (Veh-No PMF). FIG. 2 shows that TOL cells (Dig-PMF) in Ringers+$Na^+$ display about 70% of non-viable while pulsed without sodium display less than 20% of non-viable indicating that sodium is an essential participant in the TOL process ($p<0.01$).

Example 8

Figure 3:
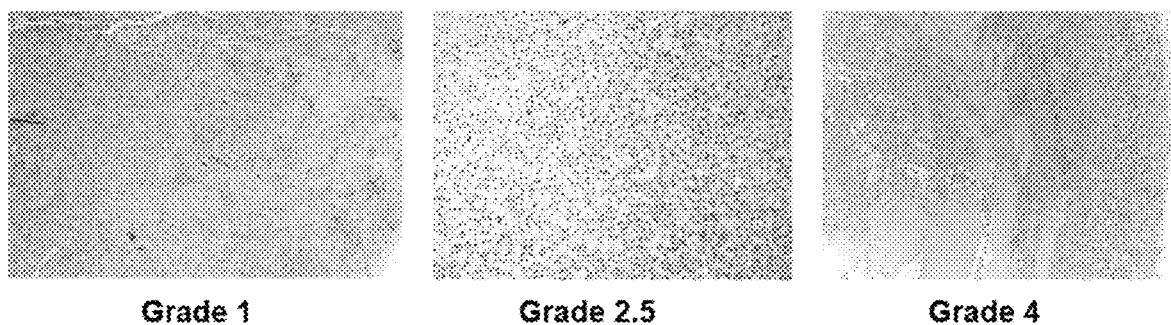
FIG. 3 Examples of H&E stained sections of MDA-MB-231 xenografts showing representative sections from tumors graded 1-5 for the level of tumor necrosis (1=normal tumor morphology; 5=total destruction).
Figure 4:
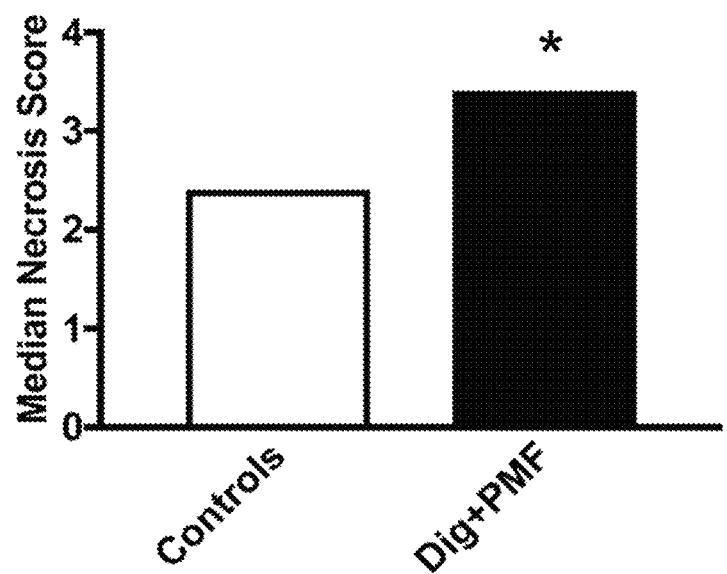
FIG. 4 The median tumor necrosis score for xenografts treated with TOL is significantly greater than the median necrosis score for xenografts treated with control, drug only, stimulation only or vehicle (control scores combined; $p<0.05$).
Figure 5:
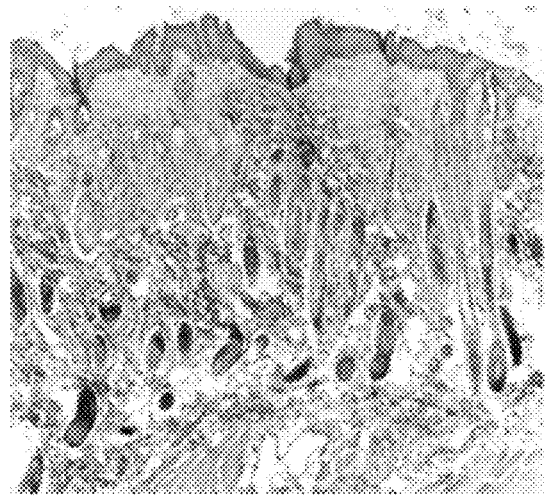
FIG. 5 TOL does not damage non-cancerous tissues. The photomicrographs illustrate sections taken from non-cancerous organs that were exposed to TOL therapy during the treatment of MDA-MB-231 xenografts. Tissues from each organs showed no signs of damage associated with TOL treatment.
Figure 5:
Figure 5:
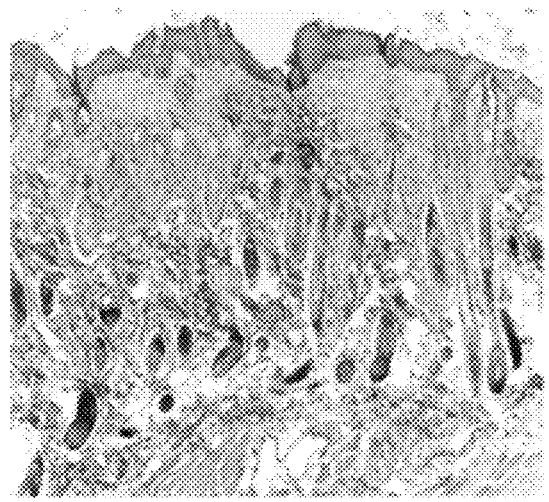
Figure 5:
Figure 6:
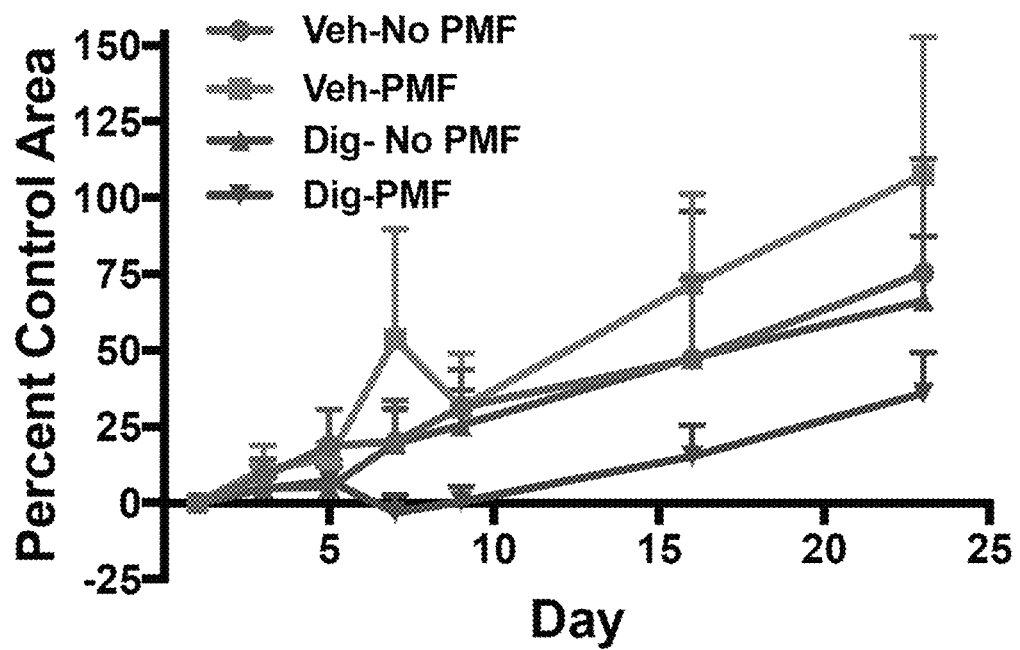
FIG. 6 Tumor growth rate is significantly slower following treatment with TOL (Dig-PMF) when compared to controls.

Results of In Vivo Studies Using Pulsed Magnetic Field (PMF) Stimulation of Voltage-Gated Sodium Channels For in vivo validation of pulsed magnetic field inducing osmotic lysis, four groups of J/Nu mice (n=8) with MDA-MB-231 xenografts (0.7–1.2 cm diameter lower back) were injected with 5 mg/kg digoxin or saline (s.c. back of neck) five times at 1 hr intervals. This protocol establishes steady-state pharmacokinetics in even poorly vascularized tissues. The mice were exposed to the pulsed magnetic field, using the same parameters as with the cultured cells, for 15 min starting 30 min after the last injection. This treatment was repeated two and four days after the first treatment. Mice were sacrificed and fixed with 4% paraformaldehyde 24 hrs after the third treatment. Tissues from these animals were sectioned and evaluated by a pathologist that was blind to the treatment. FIG. 3 shows examples of H&E stained sections of MDA-MB-231 xenografts showing representative sections from tumors graded 1-5 for the level of tumor necrosis. FIG. 4 shows that the median tumor necrosis score for xenografts treated with TOL is significantly greater than the median necrosis score for control xenografts treated with drug only, stimulation only or vehicle. Tumors from mice treated with digoxin and magnetic stimulation (TOL) showed 80-100% tumor lysis. No lysis was observed in normal muscle, kidney, brain or heart (FIG. 5). Drug-only and stimulation-only controls did not differ from untreated controls. An additional 3 immune compromised, nude mice with xenografted mesothelioma tumors showed no sign of the tumors after treatment with TOL. FIG. 6 shows that tumor growth rate is significantly slower following treatment with TOL (Dig-PMF) when compared to controls.

Example 9

Figure 7A:
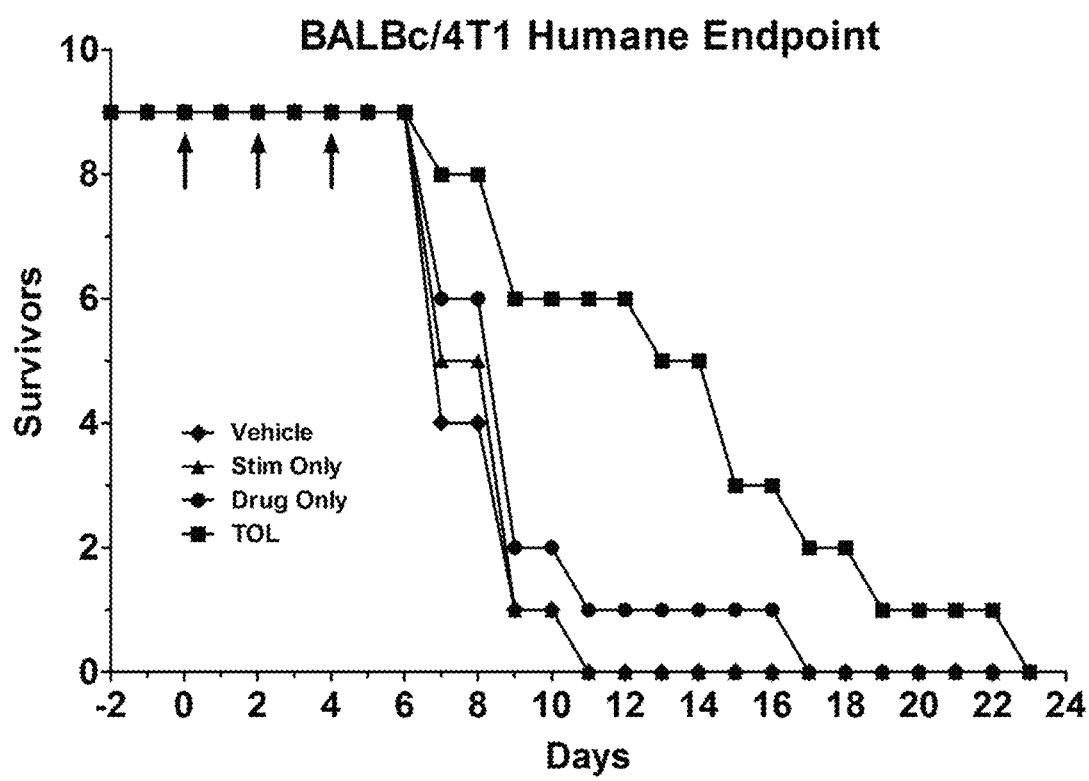
FIG. 7A. Mice treated with TOL reached humane endpoint euthanasia criteria significantly longer than mice in the control groups. Arrows indicate days of treatment; 7B. The bar graph shows that the average time until 50% of each treatment group reached humane endpoint euthanasia criteria. Thus, the life expectancy of mice treated with TOL exceeds that of controls by approximately 1 week.
Figure 7B:
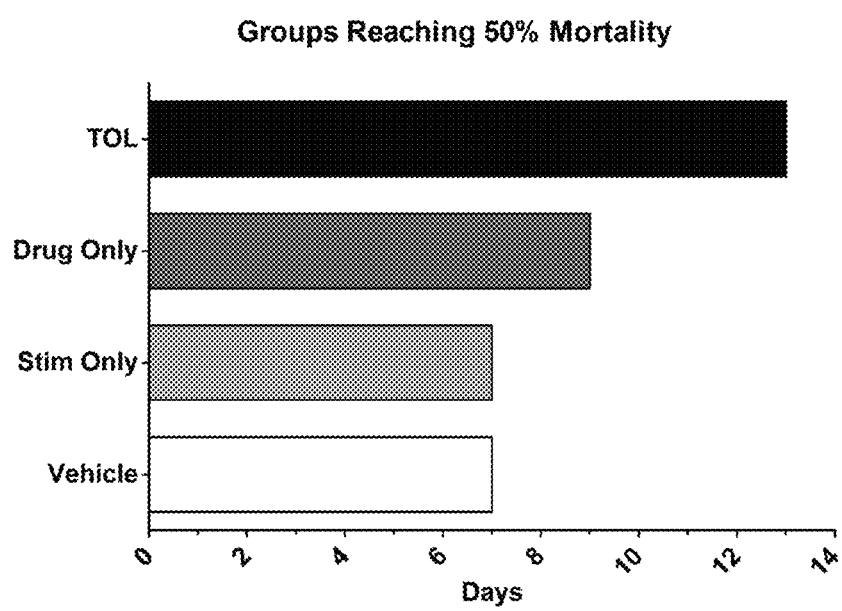

Results of In Vivo Studies Using Pulsed Magnetic Field (PMF) Stimulation of Voltage-Gated Sodium Channels in Immune Competent BALBc Mice For in vivo validation of pulsed magnetic field inducing osmotic lysis, four groups of female, immune competent BALBc mice (n=8) with xenografts (0.7–1.2 cm diameter lower back) established after injection of 500K highly malignant mouse breast cancer, 4T1, cells were injected with 7 mg/kg digoxin or saline (s.c. back of neck) five times at 1 hr intervals. This protocol establishes steady-state pharmacokinetics in even poorly vascularized tissues. The mice were exposed to the pulsed magnetic field, using the same parameters as with the cultured cells, for 30 min starting 15 min after the last injection. This treatment was administered on day 0 (first day of treatment), on day 2 and on day 4. Mice were monitored for tumor growth and were sacrificed when they met the NIH criteria for humane endpoint euthanasia. FIG. 7 shows that mice treated with TOL reached humane endpoint euthanasia criteria significantly longer than mice in the control groups.

We claim:

1. A method for treating cancer in a mammal comprising co-administering to tumor cells that over-express voltage-gated sodium channels a $Na^+$, $K^+$-ATPase inhibitor and a magnetic field capable of stimulating voltage-gated sodium channels to cause osmotic lysis of the tumor cells, wherein the magnetic field comprises a pulsed z-gradient magnetic field with a ramp rising from −90 mV to −30 mV over a rising time of about 0 to 20 msec.

2. The method of claim 1, wherein the pulsed magnetic field is a pulsed z-gradient magnetic field in the presence of a static field magnet.

3. The method of claim 1, wherein the pulsed magnetic field is a pulsed z-gradient magnetic field with a ramp rising from −90 mV to −30 mV over a rising time of about 0 to 20 msec, an inter-pulse interval of about 7.5 to 30 msec, and a pulse cycle frequency of about 20-60 PPS.

4. The method of claim 1, wherein the pulsed magnetic field is a pulsed z-gradient magnetic field with a ramp rising from −90 mV to −30 mV over a rising time of about 12.5 msec, a 7.5 msec plateau and a 12.5 msec returning to baseline where the inter-pulse interval is 7.5 msec with a pulse cycle frequency of about 25-50 PPS.

5. The method of claim 1, wherein the pulsed magnetic field is a pulsed z-gradient magnetic field with a ramp rising from −90 mV to −30 mV over a rising time of about 10 msec, returning to base over 2.5 msec, an inter-pulse interval of 7.5 msec, and a pulse cycle frequency of 25 PPS.

6. The method of claim 1, wherein the pulsed magnetic field reaches stimulus intensity at 80 mT to produces close to 100% tumor cell lysis.

7. The method of claim 1, wherein the mammal is a human.

8. The method of claim 1, wherein the tumor cells relate to a cancer selected from the group consisting of breast cancer, prostate cancer, small cell lung cancer, non-small cell lung carcinoma, lymphoma, mesothelioma, neuroblastoma, gliomas, neuromas, hepatic cancer, ovarian cancer, bladder cancer, pancreatic cancer, thyroid cancer, splenic cancer, stomach cancer, cervical cancer, skin cancers, testicular cancer, renal cancer, oral cancers, and cervical cancer.

9. The method of claim 1, wherein the tumor cells relate to breast cancer.

10. The method of claim 1, wherein the tumor cells relate to prostate cancer.

11. The method of claim 1, wherein the tumor cells relate to colon cancer.

12. The method of claim 1, wherein the tumor cells relate to small cell lung cancer.

13. The method of claim 1, wherein the tumor cells relate to non-small cell lung cancer.

14. The method of claim 1, wherein the tumor cells relate to mesothelioma.

15. The method of claim 1, wherein the inhibitor is a drug selected from the group consisting of digoxin, digitoxin, digitalis, ouabain, oleandrin, dihydroouabain, ouabain octahydrate, ouabagenin, acetyldigitoxin, acetyldigoxin, lanatoside C, deslanoside, metildigoxin, gitoformate, oleandrigenin, bufotoxin, bufotalin, marinobufagenin, palytoxin; oligomycins, rutamycin, rutamycin B, strophanthin, k-β-strophanthin, strophanthidin, k-strophanthoside, cymarin, erysimoside (cardenolide), helveticoside, peruvoside, hypothalamic sodium, potassium-adenosine triphosphatase inhibitory factor (HIF), the aglycone of HIF, arenobufagin, cinobufagin, marinobufagin, proscillaridin, scilliroside, daigremontianin, 3, 4, 5, 6-tetrahydroxyxanthone, combinations and derivatives thereof.

16. The method of claim 1, wherein the inhibitor is ouabain.

17. The method of claim 1, wherein the inhibitor is digoxin.

18. The method of claim 1, wherein the inhibitor is 3, 4, 5, 6-tetrahydroxyxanthone.

* * * * *